United States Patent [19]

Fürst et al.

[11] 4,139,716
[45] Feb. 13, 1979

[54] 19-NOR-D-HOMOPREGNANES

[75] Inventors: Andor Fürst, Basel; Jürg A. W. Gutzwiller, Bettingen; Marcel Muller, Frenkendorf, all of Switzerland; Ulrich Kerb; Rudolf Wiechert, both of Berlin, Fed. Rep. of Germany

[73] Assignee: Hoffmann-La Roche Inc., Nutley, N.J.

[21] Appl. No.: 670,211

[22] Filed: Mar. 25, 1976

[30] Foreign Application Priority Data

Apr. 9, 1975 [CH] Switzerland ............... 4499/75
Feb. 20, 1976 [CH] Switzerland ............... 2097/76

[51] Int. Cl.$^2$ .................................................. C07J 63/00
[52] U.S. Cl. .......................... 560/257; 260/340.9 AS; 260/348.52; 260/348.58; 260/408; 260/410; 260/586 E; 260/598; 424/305; 424/308; 424/311; 424/312; 424/314; 424/331; 542/402; 560/1; 560/105; 560/107; 560/122; 560/220

[58] Field of Search ........... 260/586 E, 488 B, 476 C, 260/410, 468 R, 408; 560/1, 105, 107, 122, 220, 257

[56] References Cited

U.S. PATENT DOCUMENTS

| | | | |
|---|---|---|---|
| 3,833,621 | 9/1974 | Grunwell et al. | 260/586 E |
| 3,939,193 | 2/1976 | Aliz et al. | 260/586 E |

FOREIGN PATENT DOCUMENTS 2445818  4/1975  Fed. Rep. of Germany ....... 260/586 E

OTHER PUBLICATIONS

Chem. Abstracts, 49:6299c.

*Primary Examiner*—Vivian Garner
*Attorney, Agent, or Firm*—Jon S. Saxe; George M. Gould; Raymond R. Wittekind

[57] ABSTRACT

The present disclosure relates to D-homosteroids. More particularly, the disclosure is concerned with 19-nor-D-homopregnanes, a process for the manufacture thereof and pharmaceutical preparations containing same.

5 Claims, No Drawings

19-NOR-D-HOMOPREGNANES

DESCRIPTION OF THE INVENTION

The D-homosteroids provided by the present invention have the following formula:

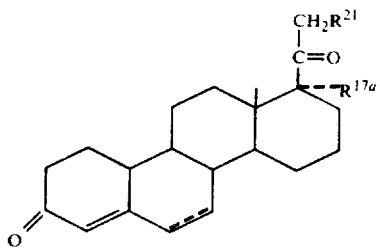

wherein $R^{17a}$ is lower alkyl, hydroxy, lower alkoxy or $C_{1-10}$ acyloxy and $R^{21}$ is hydrogen, fluorine or chlorine and wherein the broken line in the 6,7-position denotes an optional carbon-carbon bond.

As used in this specification, the term "lower" denotes that the groups prefixed therewith contain up to 7 carbon atoms. Alkyl groups and the alkyl moieties of alkoxy groups can be straight-chain or branched-chain. Examples of lower alkyl groups are methyl, ethyl, propyl, isopropyl, butyl and isomers thereof, pentyl, neopentyl, hexyl and heptyl. Preferred lower alkyl groups contain from 1 to 4 carbon atoms.

An acyloxy group can be derived from a saturated or unsaturated aliphatic carboxylic acid, a cycloaliphatic, araliphatic or aromatic carboxylic acid preferably containing up to 10 carbon atoms. Examples of such acids are formic acid, acetic acid, pivalic acid, propionic acid, butyric acid, caproic acid, oenanthic acid, decyclic acid, cyclopentylpropionic acid, cyclohexylpropionic acid, phenylacetic acid and benzoic acid. Especially preferred acyloxy groups are alkanoyloxy groups containing from 1 to 7 carbon atoms.

Of particular interest are D-homosteroids of formula I in which $R^{21}$ is hydrogen. Further, those D-homosteroids of formula I in which $R^{17a}$ is alkanoyloxy containing from 1 to 7 carbon atoms are of high interest. A further interesting group of D-homosteroids of formula I comprises those which are saturated in the 6,7-position.

According to the process aspects provided by the present invention, the D-homosteroids of formula I hereinbefore are prepared by (a) oxidizing a $\Delta^4$-, $\Delta^5$- or $\Delta^{5(10)}$-D-homosteroid of the formula

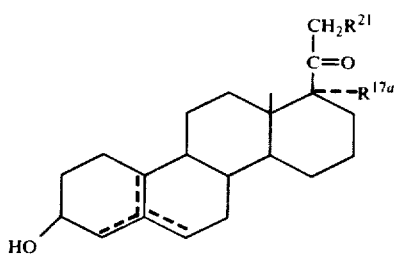

wherein $R^{17a}$ and $R^{21}$ have the significance given earlier and one of the double bonds denoted by broken lines and emanating from the carbon atom in the 5-position is present;

or (b) hydrolysing a D-homosteroid of the general formula

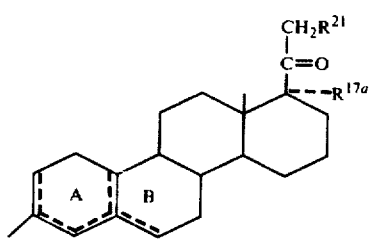

, wherein $R^{17a}$ and $R^{21}$ have the significance given earlier, X represents an organic residue bound to the ring system via a nitrogen atom or at least one oxygen or sulphur atom and the broken lines in rings A and B denote that one additional carbon-carbon bond can be present within this ring system, with the formation of a $\Delta^4$-3,20-diketone; or (c) oxidising a D-homosteroid of the general formula

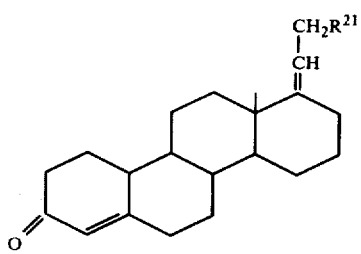

, wherein $R^{21}$ has the significance given earlier, to the corresponding 17aα-hydroxy-3,20-diketone; or (d) replacing the 21-hydroxy group in a D-homosteroid of the general formula

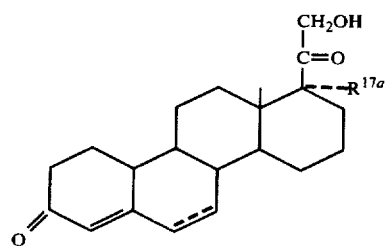

, wherein $R^{17a}$ and the broken line in the 6,7-position have the significance given earlier, by a chlorine or bromine atom; or (e) cleaving off the 10-formyl group from a D-homosteroid of the general formula

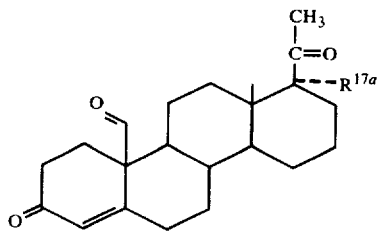

, wherein $R^{17a}$ has the significance given earlier;

or (f) dehydrating or dehydrohalogenating a D-homosteroid of the general formula

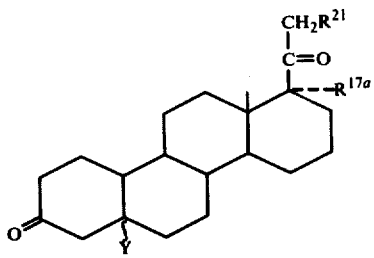

(VII)

, wherein $R^{17a}$ and $R^{21}$ have the significance given earlier and Y is hydroxy or halogen or (g) reductively alkylating a D-homosteroid of the formula

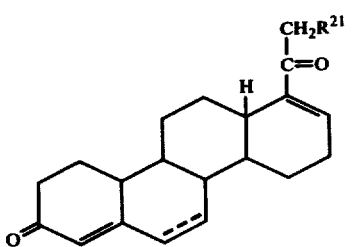

(VIII)

, wherein $R^{21}$ and the broken line in the 6,7-position have the significance given earlier,
with the intermediate protection of the 3-keto group; or (h) hydroxylating a D-homosteroid of the formula

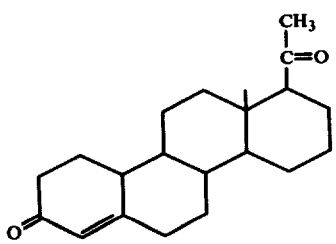

(IX)

in the 17a-position with intermediate protection of the 3-keto group;

or (i) dehydrogenating a 6,7-saturated D-homosteroid of formula I in the 6,7-position; or (j) appropriately alkylating or acylating a 17a-hydroxy group in a D-homosteroid of formula I.

The starting materials of formula II contain a $\Delta^4$-, $\Delta^5$- or a $\Delta^{5(10)}$-double bond. In carrying out embodiment (a) of the process a D-homosteroid of formula II, preferably one which contains a $\Delta^5$-double bond, is oxidised, for example, according to the Oppenauer procedure (e.g. using aluminium isopropylate, $Al[OCH(CH_3)_2]_3$) or by means of chromic acid (e.g. Jones reagent) or according to the Pfitzner-Moffatt procedure (using dimethylsulphoxide/dicyclohexylcarbodiimide, the initially obtained $\Delta^5$-3-ketone requiring subsequent isomerisation to the $\Delta^4$-3-ketone) or by means of pyridine/sulphur trioxide in dimethylsulphoxide. When the aforementioned oxidising agents are used, the product obtained contains a 3-keto-$\Delta^4$-grouping. When oxidising agents such as bromine/lithium bromide/lithium carbonate in dimethylformamide are used or when the oxidation is carried out according to the Oppenauer procedure in the presence of benzoquinone, the oxidation yields a product containing a 3-keto-$\Delta^{4,6}$-grouping.

Examples of D-homosteroid starting materials of formula III are those in which X together with the double bonds in the rings A and/or B represents a 3-alkoxy (e.g. 3-methoxy)-$\Delta^{2,5(10)}$-, 3-alkylthio (e.g. 3-methylthio)-$\Delta^{2,5(10)}$-, 3-sec.amino (e.g. pyrrolidino)-$\Delta^{2,5(10)}$-, 3,3-alkylenedioxy (e.g. ethylenedioxy)-$\Delta^{5(10)}$-, -$\Delta^4$- or -$\Delta^5$-, or 3,3-alkylenedithio (e.g. ethylenedithio)-$\Delta^{5(10)}$-, $\Delta^4$- or -$\Delta^5$-grouping. Preferred groups denoted by X are lower alkyl or lower alkylene residues bound via a nitrogen atom or at least one oxygen or sulphur atom, i.e., sec.amino, ether, thioether, ketal and thioketal functions.

The hydrolysis of a D-homosteroid starting material of formula III in accordance with embodiment (b) of the process can be carried out in a manner known per se using an acid (e.g. a mineral acid such as hydrochloric or a carboxylic acid such as oxalic acid) or, in the case of 3,3-alkylenedithio-substituted starting materials, using heavy metal ions such as $Hg^{++}$ or $Cd^{++}$. As the medium in which the hydrolysis is carried out there are especially suitable aqueous-alcoholic solutions (e.g. methanol/water) which may contain further solvent (e.g. chloroform).

The oxidation of the 17a(20)-double bond in a D-homosteroid starting material of formula IV in accordance with embodiment (c) of the process can be carried out, for example, using an oxidising agent such as a tertiary amine N-oxide peroxide and hydrogen peroxide in tert.butanol/pyridine in the presence of catalytic amount of osmium tetroxide. Examples of tertiary amine N-oxide peroxides are N-methylmorpholine N-oxide peroxide and triethylamine oxide peroxide. Alternatively, the oxidation can be carried out using an oxidising agent such as osmium tetroxide or permanganate to give a 17a,20-glycol which is further oxidised to a hydroxy ketone using an oxidising agent such as dimethylsulphide or N-chlorosuccinimide or using dimethylsulphoxide and chlorine.

The replacement of the 21-hydroxy group in a D-homosteroid starting material of formula V in accordance with embodiment (d) of the process can be carried out via the mesylate of tosylate by reaction thereof with an alkali metal halide (e.g. sodium fluoride, sodium chloride or lithium chloride) or with carbon tetrachloride and triphenylphosphine in dimethylformamide.

The cleavage of the 10-formyl group from a D-homosteroid starting material of formula VI in accordance with embodiment (e) of the process can be carried out, for example, by treatment with a base (e.g. an alcoholic alkali metal hydroxide solution such as methanolic sodium hydroxide or potassium hydroxide), conveniently at a temperature below room temperature and under the atmosphere of an inert gas.

The dehydration or dehydrohalogenation in accordance with embodiment (f) of the process, i.e. the cleavage of HY from a D-homosteroid starting material of formula VII, preferably one in which Y represents a hydroxy group or a fluorine, chlorine or bromine atom and especially one in which Y represents a hydroxy group or a bromine atom, can be carried out in a manner known per se. The dehydration can be carried out by treatment with an acid (e.g. a mineral acid such as hydrochloric acid) or with a base. The dehydrohalogenation can likewise be carried out by means of an acid or base (e.g. an organic base such as pyridine).

Embodiment (g) of the process can be carried out in a manner known per se for the reductive alkylation of conjugated enones; for example, in ammonia/tetrahydrofuran using lithium and the corresponding alkyl iodide. The 3-keto group can be protected, for example, by ketalisation or by reduction to the hydroxy group, whereby after the alkylation the keto group can be regenerated in a manner known per se from a ketal group (e.g. an ethylenedioxy group) by means of dilute acid or from a hydroxy group by chromic acid oxidation.

The hydroxylation of a D-homosteroid starting material of formula IX in accordance with embodiment (h) of the process can be carried out in a manner known per se by using a strong base such as a tert.butylate in tert-.butanol and oxygen in a solvent such as dimethylformamide. The 3-keto group can be protected and subsequently regenerated as described in connection with embodiment (g) hereinbefore.

The 6,7-dehydrogenation of a 6,7-saturated D-homosteroid of formula I in accordance with embodiment (i) of the process can be carried out using a dehydrogenating agent known to be suitable for the 6,7-dehydrogenation of steroids such as substituted benzoquinones (e.g. chloranil or dichlorodicyanobenzoquinone) or using manganese dioxide.

The alkylation and acylation of a 17a-hydroxy group in a D-homosteroid of formula I in accordance with embodiment (i) of the process can be carried out in a manner known per se. The alkylation can be carried out, for example, by treatment with an alkyl halide such as methyl or ethyl iodide in the presence of a base such as pyridine. The acylation can be carried out, for example, by treatment with a reactive acid derivative such as an acid halide or anhydride in the presence of the acid corresponding to the acylating agent and a strong acid such as p-toluenesulphonic acid, perchloric acid or a mineral acid such as hydrochloric acid.

The D-homosteroid starting materials aforesaid, insofar as their preparation is not described herein, can be prepared in analogy to the methods described in the Examples hereinafter.

The D-homosteroids of formula I hereinbefore possess hormonal activity, especially on the endocrine system, and are characterised by a selectivity of the activity. They can accordingly be used as hormonally-active agents (e.g. as progestatives) and can be administered orally or parenterally. In general, dosages of 0.005 mg/kg to 0.15 mg/kg per day can be administered. The D-homosteroid 17a-acetoxy-19-nor-D-homo-4-pregnene-3,20-dione, for example, shows the following McPhail values in the Clauberg test upon subcutaneous administration:

| Dosage [μg] | McPhail index |
|---|---|
| 0.2 | 0.2 |
| 1.0 | 2.7 |
| 5.0 | 4 |

The D-homosteroids of formula I can be used as medicaments, e.g. in the form of pharmaceutical preparations having direct or delayed liberation of the active ingredient which contain them in association with a compatible pharmaceutical carrier material. This carrier material can be an organic or inorganic inert carrier material suitable for enteral, percutaneous or parenteral administration such as water, gelatine, gum arabic, lactose, starch, magnesium stearate, talc, vegetable oils, polyalkyleneglycols, petroleum jelly etc. The pharmaceutical preparations can be made up in a solid form (e.g. as tablets, dragées, suppositories or capsules), in a semi-solid form (e.g. as salves) or in a liquid form (e.g. as solutions, suspensions or emulsions). If necessary, the pharmaceutical preparations can be sterilised and/or can contain adjuvant substances such as preserving, stabilising, wetting or emulsifying agents, salts for the variation of the osmotic pressure or substances acting as buffers. They can also contain still other therapeutically valuable substances.

The pharmaceutical preparations can be prepared in a manner known per se by mixing a D-homosteroid of formula I with non-toxic solid and/or liquid carrier materials and adjuvants which are customary in pharmaceutical preparations and which are suitable for therapeutic administration (e.g. those carrier materials and adjuvants mentioned earlier) and transforming the mixture into the desired pharmaceutical dosage form.

EXAMPLE 1

680 mg of 17a-acetoxy-3,20-dioxo-D-homo-4-pregnen-19-al are dissolved in 34 ml of methylene chloride, cooled in an ice-bath under a nitrogen stream and treated with a likewise-cooled solution of 2.04 g of sodium hydroxide in 136 ml of methanol. The mixture is then stirred for 2.5 hours at ice-bath temperature and under a nitrogen stream, subsequently diluted with ether, washed with water, dried and evaporated. The residue is chromatographed on silica gel and recrystallised from diisopropyl ether. There are obtained 350 mg of 17a-acetoxy-19-nor-D-homo-4-pregnene-3,20-dione of melting point 200.5°–202.5° C.; UV: $\epsilon_{240} = 17300$.

The starting material can be prepared as follows:

50.0 g of 3β-hydroxy-D-homo-5,17-pregnadien-20-one are dissolved in 500 ml of methylene chloride, 750 ml of ethanol and 3.5 liters of methanol and treated at 35° C. with 40 ml of 4-N sodium hydroxide and 50 ml of 30% hydrogen peroxide. After a reaction time of 4 days at 35° C., 40 ml of 30% hydrogen peroxide being added twice daily, the solution is extensively concentrated in vacuo at 35° C., subsequently diluted with methylene chloride and washed free from hydrogen peroxide with water. After drying over sodium sulphate, the mixture is evaporated to dryness in vacuo and the residue stirred at 60° C. for 30 minutes in 200 ml of pyridine and 100 ml of acetic acid anhydride. The precipitate obtained after precipitation with ice-water is filtered off under suction, washed well with water, taken up in methylene chloride and dried. After chromatography on silica gel, there are obtained, after recrystallisation from diisopropyl ether, 21.3 g of 3β-acetoxy-17α,17a-epoxy-D-homo-5-pregnen-20-one of melting point 161°–163° C.

14.0 g of 3β-acetoxy-17α,17a-epoxy-D-homo-5-pregnen-20-one in 140 ml of acetic acid are treated with 42 g of lithium bromide and the mixture is stirred at room temperature for 2 days. The mixture is stirred into ice-water, the precipitate filtered off, washed well with water, taken up in methylene chloride and dried. After evaporation, there are obtained 17.4 g of crude 3β-acetoxy-17β-bromo-17a-hydroxy-D-homo-5-pregnen-20-one.

17.4 g of crude 3β-acetoxy-17β-bromo-17a-hydroxy-D-homo-5-pregnen-20-one are dissolved in 174 ml of benzene and 174 ml of tetrahydrofuran. 17.4 ml of tributyltin hydride and 870 mg of α,α'-azobisisobutyronitrile are added under a nitrogen stream and the mixture is stirred at 60° C. for 1.5 hours. The mixture is then extensively concentrated in vacuo, the residue treated with pentane, the precipitate filtered off under suction and recrystallised from ethyl acetate. There are obtained 11.6 g of 3β-acetoxy-17a-hydroxy-D-homo-5-pregnen-20-one of melting point 208°–210.5° C.

7.25 g of 3β-acetoxy-17a-hydroxy-D-homo-5-pregnen-20-one are stirred at room temperature for 18 hours in 36 ml of acetic acid, 11 ml of acetic acid anhydride and 1.45 g of p-toluene-sulphonic acid. The precipitate obtained after precipitation with ice-water and filtration is taken up in methylene chloride, dried and evaporated. There are obtained 7.1 g of 3β,17a-diacetoxy-D-homo-5-pregnen-20-one of melting point 126°–127° C. (recrystallisation from methanol).

10.0 g of 3β,17a-diacetoxy-D-homo-5-pregnen-20-one are dissolved in 300 ml of dioxane and to the resulting solution are successively added 30 ml of water, 10 g of N-bromosuccinimide and 3 ml of 70% perchloric acid. The mixture is then stirred at room temperature for 1.5 hours and stirred into ice-water with the addition of sodium hydrogen sulphite. The precipitate formed is filtered off under suction, washed well and dried at room temperature in vacuo. There are obtained 12.3 g of crude 5-bromo-3β,17a-diacetoxy-6β-hydroxy-D-homo-5α-pregnen-20-one.

12.3 g of crude 5-bromo-3β,17a-diacetoxy-6β-hydroxy-D-homo-5α-pregnan-20-one in 615 ml of absolute benzene are heated under reflux for 30 minutes with 13.5 g of lead tetraacetate and 6.15 g of iodine. The mixture is then diluted with benzene, washed with water, sodium hydrogen sulphite solution, sodium hydrogen carbonate solution and water. After evaporation, the residue is chromatographed on silica gel and yields 4.6 g of crude 5-bromo-3β,17a-diacetoxy-6β,19-epoxy-D-homo-5α-pregnan-20-one. A sample recrystallised from diisopropyl ether/acetone melts at 213.5°–219° C.

4.0 g of crude 5-bromo-3β, 17a-diacetoxy-6β, 19-epoxy-D-homo-5α-pregnan-20-one in 80 ml of acetic acid are stirred at room temperature for 3.5 hours with 20 g of zinc dust. The mixture is then separated from the zinc dust through a frit and washed well with methylene chloride. The filtrate is extensively concentrated in vacuo, the residue taken up in methylene chloride and washed with sodium hydrogen carbonate solution and water. After evaporation, the residue is chromatographed on silica gel and recrystallised from diisopropyl ether. There are obtained 465 mg of 3β,17a-diacetoxy-19-hydroxy-D-homo-5-pregnen-20-one of melting point 149°–152.5° C.

3.3 g of crude 3β,17a-diacetoxy-19-hydroxy-D-homo-5-pregnen-20-one, obtained after chromatography, are stirred at room temperature for 1 hour in 33 ml of absolute tetrahydrofuran with 3.3 ml of dihydropyran and 0.05 ml of phosphorus oxychloride. The mixture is then diluted with ether, washed with sodium hydrogen carbonate solution and water, dried and evaporated. The residue is chromatographed on silica gel and yields 1.95 g of 3β,17a-diacetoxy-19-(tetrahydropyran-2-yloxy)-D-homo-5-pregnen-20-one as an oil.

1.95 g of 3β,17a-diacetoxy-19-(tetrahydropyran-2-yloxy)-D-homo-5-pregnen-20-one in 19.5 ml of methanol are heated at reflux for 15 minutes with 1.95 ml of water and 975 mg of potassium carbonate. The mixture is then diluted with ether, washed with water and dried. After evaporation, there are obtained 1.8 g of crude 17a-acetoxy-3β-hydroxy-19-(tetrahydropyran-2-yloxy)-D-homo-5-pregnen-20-one.

1.8 g of crude 17a-acetoxy-3β-hydroxy-19-(tetrahydropyran-2-yloxy)-D-homo-5-pregnen-20-one in 36 ml of absolute toluene and 1.8 ml of cyclohexanone are treated with a solution of 900 g of aluminium isopropylate in 5 ml of absolute toluene and the mixture is heated for 1 hour with slow distillation. The mixture is then diluted with ether, washed with dilute sulphuric acid and water, dried and evaporated. There are obtained 1.85 g of crude 17a-acetoxy-19-(tetrahydropyran-2-yloxy)-D-homo-4-pregnene-3,20-dione.

1.8 g of 17a-acetoxy-19-(tetrahydropyran-2-yloxy)-D-homo-4-pregnene-3,20-dione in 36 ml of methanol and 9 ml of water are heated at reflux for 30 minutes with 900 mg of oxalic acid. The mixture is then taken up with ether, washed with water, dried and evaporated. After chromatography on silica gel, there are obtained 830 mg of crude 17a-acetoxy-19-hydroxy-D-homo-4-pregnene-3,20-dione. A sample recrystallised from diisopropyl ether/acetone melts at 223.5°–226.5° C.; UV: $\epsilon_{242} = 15000$.

800 mg of crude 17a-acetoxy-19-hydroxy-D-homo-4-pregnene-3,20-dione in 40 ml of pyridine are treated with a solution of 2.5 g of chromium trioxide in 25 ml of water and 50 ml of pyridine and the mixture is stirred at 50° C. for 2.5 hours. Thereafter, the mixture is stirred into ice-water, extracted with ether, the combined organic phases are washed with water, dilute sulphuric acid and water, dried and evaporated. There are obtained 680 mg of crude 17a-acetoxy-3,20-dioxo-D-homo-4-pregnen-19-al.

EXAMPLE 2

1.4 g of 17a-hexanoyloxy-3,20-dioxo-D-homo-4-pregnen-19-al are deformylated as described in Example 1 with sodium hydroxide in methanol/methylene chloride and yield 800 mg of 17a-hexanoyloxy-19-nor-D-homo-4-pregnene-3,20-dione; UV: $\epsilon_{240} = 17600$; melting point 109.5°–110.5° C. (from diisopropyl ether).

The starting material can be prepared as follows:

20 g of 3β-acetoxy-17a-hydroxy-D-homo-5-pregnen-20-one in 100 ml of absolute benzene are stirred at room temperature for 30 minutes with 22 ml of caproic acid anhydride and 0.04 ml of 70% perchloric acid. The mixture is then diluted with ether, washed with water and concentrated. The residue is distilled with steam and the product further isolated via a methylene chloride extract. After chromatography on silica gel, there are obtained 23.1 g of 3β-acetoxy-17a-hexanoyloxy-D-homo-5-pregnen-20-one as an oil.

20.0 g of 3β-acetoxy-17a-hexanoyloxy-D-homo-5-pregnen-20-one in 600 ml of dioxane are treated successively with 60 ml of water, 20 g of N-bromosuccinimide and 6 ml of 70% perchloric acid and the mixture is stirred at room temperature for 15 minutes. The mixture is then stirred into ice-water with the addition of sodium hydrogen sulphite. The precipitate is filtered off under suction, washed and dried and yields 23 g of crude 3β-acetoxy-5-bromo-17a-hexanoyloxy-6β-hydroxy-D-homo-5α-pregnan-20-one.

23 g of crude 3β-acetoxy-5-bromo-17a-hexanoyloxy-6β-hydroxy-D-homo-5α-pregnan-20-one in 1.15 liters of absolute benzene are heated under reflux for 30 minutes with 11.5 g of iodine and 25.2 g of lead tetraacetate.

After working-up in accordance with Example 1, there are obtained 13.5 g of crude 3β-acetoxy-5-bromo-17a-hexanoyloxy-6β,19-epoxy-D-homo-5α-pregnan-20-one. A sample recrystallised from diisopropyl ether/acetone melts at 160°–161° C.

In accordance with Example 1, 12 g of crude 3β-acetoxy-5-bromo-17a-hexanoyloxy-6β,19-epoxy-D-homo-5α-pregnan-20-one are reacted with zinc dust in acetic acid and worked-up. After chromatography on silica gel, there are obtained 8.5 g of 3β-acetoxy-17a-hexanoyloxy-19-hydroxy-D-homo-5-pregnan-20-one.

As described in Example 1, 8.5 g of 3β-acetoxy-17a-hexanoyloxy-19-hydroxy-D-homo-5-pregnan-20-one are reacted with dihydropyran and worked-up. There are obtained 5.5 g of 3β-acetoxy-17a-hexanoyloxy-19-(tetrahydropyran-2-yloxy)-D-homo-5-pregnan-20-one.

5.5 g of 3β-acetoxy-17a-hexanoyloxy-19-(tetrahydropyran-2-yloxy)-D-homo-5-pregnen-20-one are saponified with potassium carbonate as described in Example 1 and yield 5 g of 17a-hexanoyloxy-3β-hydroxy-19-(tetrahydropyran-2-yloxy)-D-homo-5-pregnen-20-one.

5 g of 17a-hexanoyloxy-3β-hydroxy-19-(tetrahydropyran-2-yloxy)-D-homo-5-pregnen-20-one are oxidised according to the Oppenauer procedure as described in Example 1 and yield 4.8 g of 17a-hexanoyloxy-19-(tetrahydropyran-2-yloxy)-D-homo-4-pregnene-3,20-dione.

4.8 g. of 17a-hexanoyloxy-19-(tetrahydropyran-2-yloxy)-D-homo-4-pregnene-3,20-dione are saponified with oxalic acid as described in Example 1. There are obtained 2.1 g of 17a-hexanoyloxy-19-hydroxy-D-homo-4-pregnene-3,20-dione; UV: $\epsilon_{242}$ = 14600; melting point 146.5°–148° C.

2.0 g of 17a-hexanoyloxy-19-hydroxy-D-homo-4-pregnene-3,20-dione are oxidised with pyridine/chromic acid as described in Example 1. There are obtained 1.4 g of 17a-hexanoyloxy-3,20-dioxo-D-homo-4-pregnen-19-al.

EXAMPLE 3

A solution of 8.5 g of D-homo-19-norpregna-4,17a(20)-dien-3-one in 40 ml of methylene chloride, 70 ml of tert.-butanol and 12 ml of pyridine is treated with 100 mg of osmium tetroxide and with 30 ml of N-methylmorpholine oxide reagent (9.4 ml of 70% hydrogen peroxide added dropwise to 10 g of N-methylmorpholine in 115 ml of tert.butanol, treated after 68 hours with 22.5 g of sodium sulphate, stirred for 24 hours and separated from salt by filtration). After stirring under argon for 16 hours in the dark at 25° C., a further 20 ml of N-methylmorpholine oxide reagent are added and the mixture is stirred for a further 24 hours. Thereafter, 10 g of sodium sulphite are added, the mixture is stirred for 90 minutes, poured on to ice-water and extracted four times with methylene chloride. The organic phases are washed twice with water, dried over sodium sulphate and evaporated to dryness. The crude product (9.5 g) is adsorbed on 300 g of silica gel (Merck, 0.06–0.2 mm). Elution with hexane/ethyl acetate (4:1) yields a product from which, by further column chromatography, there is obtained pure 17a-hydroxy-D-homo-19-norpregn-4-ene-3,20-dione of melting point 227°–228° C.; $[\alpha]_D^{25}$ = ±0° (c = 1.0 in chloroform).

The starting material can be prepared as follows:

D-Homooestrone methyl ether is converted by a Wittig reaction into the corresponding 17a-ethylidene compound. Birch reduction and subsequent acid hydrolysis yields D-homo-19-norpregna-4,17a(20)-dien-3-one as a ca 1:1 mixture of two geometric isomers; melting point 123°–127° C.; $[\alpha]_D^{25}$ = −40.7° (c = 1.0 in chloroform).

EXAMPLE 4

A solution of 0.45 g of 17a-hydroxy-D-homo-19-norpregn-4-ene-3,20-dione in 20 ml of glacial acetic acid and 4 ml of acetic anhydride is treated with 0.1 g of p-toluenesulphonic acid and stirred under argon at 25° C. for 18 hours. Thereafter, the mixture is poured on to ice/1-N sodium hydroxide and extracted three times with methylene chloride. The organic extracts are washed with water, dried over sodium sulphate and evaporated. The crude product (0.52 g) is adsorbed on 50 g of silica gel. Elution with methylene chloride yields 0.81 g of 17a-acetoxy-D-homo-19-norpregn-4-ene-3,20-dione of melting point 201°–202° C.; $[\alpha]_{589}^{25}$ = +15° (c = 0.104 in dioxane).

EXAMPLE 5

0.54 g of 3β,17a-dihydroxy-D-homo-19-norpregn-5(10)-en-20-one are dissolved in 50 ml of toluene, treated with 10 ml of cyclohexanone and with 1 g of aluminium isopropylate and the mixture is heated under slight reflux for 4 hours. The cooled mixture is treated with 2 ml of water. The precipitated aluminium salts are removed by filtration and back-washed with toluene. The crystalline residue obtained after evaporation of the filtrate yields, after crystallisation from methylene chloride/ether, pure 17a-hydroxy-D-homo-19-norpregn-4-ene-3,20-dione of melting point 227°–228° C.

The starting material can be prepared as follows:

D-Homooestrone methyl ether is converted into the 17a-ethylidene compound by a Wittig reaction using triphenylethylidene phosphorane. Birch reduction, mild acidic hydrolysis with aqueous oxalic acid and subsequent sodium borohydride reduction yields 3β-hydroxy-D-homo-19-norpregna-5(10),17a(20)-diene which is subjected to oxidation with N-methylmorpholine oxide/hydrogen peroxide/osmium tetroxide as described in Example 3. After separation of the mixture on silica gel, there is obtained 3β,17a-dihydroxy-D-homo-19-norpregn-5(10)-en-20-one.

EXAMPLE 6

A solution of 1.5 g of 3,3-ethylenedioxy-17a-hydroxy-D-homo-19-norpregn-5(10)-en-20-one in 100 ml of 90% aqueous acetone is treated with 5 ml of concentrated hydrochloric acid and stirred at 25° C. for 6 hours. After neutralisation with aqueous bicarbonate solution, the acetone is removed on a rotary evaporator and the residue partitioned between methylene chloride and water. Usual working-up yields crystalline, crude 17a-hydroxy-D-homo-19-norpregn-4-ene-3,20-dione which is recrystallised from methylene chloride/ether; melting point 227°–229° C.

The starting material can be prepared as follows:

D-Homooestrone methyl ether is converted into 3-methoxy-D-homo-19-norpregna-2,5(10),17a(20)-triene by a Wittig reaction and Birch reduction. Ketalisation using ethyleneglycol in glacial acetic acid/methylene chloride and subsequent oxidation with N-methylmorpholine oxide/hydrogen peroxide/osmium tetroxide (as described in Example 3) yields, after chromatography on silica gel, 3,3-ethylenedioxy-17a-hydroxy-D-homo-19-norpregn-5(10)-en-20-one.

EXAMPLE 7

3.1 g of 17a,21-dihydroxy-D-homo-19-norpregn-4-ene-3,20-dione are dissolved in 50 ml of pyridine and treated at 0° C. while stirring with 2 ml of methanesulphonyl chloride. After 3 hours at 25° C., the mixture is evaporated to dryness on a rotary evaporator, treated with methylene chloride and aqueous bicarbonate solution and worked-up in the usual manner. The crude mesylate and 3.5 g of potassium fluoride in 100 ml of dimethylformamide are heated to 100° C. for 18 hours. After evaporation of the solvent in vacuo, the residue is partitioned between methylene chloride and water and worked-up in the usual manner. From the crude product there is obtained, after chromatography on silica gel, pure 21-fluoro-17a-hydroxy-D-homo-19-norpregn-4-ene-3,20-dione.

The starting material can be prepared as follows:

3,3-Ethylenedioxy-17a-hydroxy-D-homo-19-norpregn-5(10)-en-20-one is converted in a known manner (1. iodine/calcium oxide/calcium chloride/methanol; 2. potassium acetate/acetone) into the corresponding 21-acetoxy compound which, after hydrolysis, yields 17a,21-dihydroxy-D-homo-19-norpregn-4-ene-3,20-dione.

EXAMPLE 8

A solution of 8.3 g of D-homo-19-norpregna-4,17-diene-3,20-dione in 120 ml of orthoformic acid ethyl ester and 10 ml of ethanol is treated while stirring at 0° C. with 1 g of solid p-toluenesulphonic acid. After 90 minutes, the mixture is partitioned between ether and aqueous bicarbonate solution and worked-up in the usual manner. The crude 3-ethoxy-D-homo-19-norpregna-3,5,17-trien-20-one is dissolved in 200 ml of tetrahydrofuran, treated with 1.4 g of tert.butanol and stirred into a blue solution, cooled to −40° C., of 0.7 g of lithium in 250 ml of liquid ammonia. After stirring for 30 minutes at −40° C., the mixture is treated with 12 ml of methyl iodide and, after stirring for a further 30 minutes, the ammonia is distilled off at normal pressure. The residue is partitioned between ether and water and worked-up in the usual manner. The crude product is dissolved in 200 ml of methanol, treated with 20 ml of 1-N aqueous hydrochloric acid and stirred at 25° C. for 60 minutes. After neutralisation with ammonium hydroxide, the methanol is removed on a rotary evaporator and the aqueous residue is extracted with ether. After the usual worked-up and chromatography on silica gel, there is obtained 17a-methyl-D-homo-19-norpregn-4-ene-3,20-dione; UV: $\lambda_{max}$ = 241 nm ($\epsilon$ = 16800).

The starting material can be prepared as follows:

76.5 ml of a ca 20–25% solution of n-butyllithium in hexane are stirred into a solution of 27.7 ml of N-cyclohexyl-isopropylamine in 100 ml of tetrahydrofuran at −78° C. under argon. 150 ml of this solution are stirred within 2 hours under argon into a solution, cooled to −78° C., of 20 g of D-homooestrone methyl ether in 100 ml of methylene chloride. After stirring for a further 2 hours at −78° C., the mixture is treated with a solution of 10 g of ammonium chloride in 50 ml of water, the aqueous phase is made acid by the addition of 1-N hydrochloric acid and extracted with methylene chloride. The organic solution is washed with saturated bicarbonate solution and with water, dried over sodium sulphate and evaporated to dryness. The crude product is dissolved in 100 ml of toluene, heated at reflux for 4 hours and the residue obtained after evaporation adsorbed on 600 g of silica gel. Elution with hexane/ethyl acetate (9:1 vol/vol) yields 20.8 g of 17a-chloro-3-methoxy-D-homooestra-1,3,5(10)-triene-17aβ-carboxaldehyde of melting point 116°–117° C. (from methylene chloride/hexane); $[\alpha]_{589}^{25}$ = −5° (c = 0.101 in dioxane).

A solution of 20.8 g of 17a-chloro-3-methoxy-D-homooestra-1,3,5(10)-triene-17aβ-carboxaldehyde in 25 ml of hexamethylphosphoric acid triamide is treated with 2.5 g of lithium chloride and the mixture is stirred at 50° C. for 12 hours with the portionwise and gradual addition of 5 g of sodium bicarbonate. After standing overnight at 25° C., the mixture is treated with ether, washed three times with water and once with saturated bicarbonate solution, dried over sodium sulphate and concentrated. The residue is adsorbed on 1 kg of silica gel. Elution with methylene chloride yields 10.1 g of 3-methoxy-D-homooestra-1,3,5(10),17-tetraene-17a-carboxaldehyde of melting point 126°–127° C. (from acetone/ether); $[\alpha]_{589}^{25}$ = +207° (c = 0.100 in dioxane).

45 ml of a ca 2 molar solution of methyllithium in ether is added at 0° C. under argon and while stirring to a solution of 18 g of 3-methoxy-D-homooestra-1,3,5(10),17-tetraene-17a-carboxaldehyde in 250 ml of absolute tetrahydrofuran. After 2 hours, the mixture is treated with aqueous ammonium chloride solution and extracted 4 times with ether. The organic phases are washed twice with sodium carbonate solution, dried over sodium sulphate and concentrated. The crude product is dissolved in 400 ml of tert.butanol and 400 ml of tetrahydrofuran and added dropwise to 1.2 liters of anhydrous ammonia. The boiling solution is treated portionwise with 6.1 g of sodium. After 2.5 hours, the ammonia is distilled off, the mixture concentrated and partitioned between ether and water. After drying over sodium sulphate, the solution is concentrated. The residue is dissolved in 50 ml of methylene chloride, treated with 100 ml of ethyleneglycol and 25 ml of glacial acetic acid and stirred at 25° C. for 18 hours. The mixture is poured into ice-cold 3-N sodium hydroxide, extracted with ether and, after washing with water and drying over sodium sulphate, concentrated on a rotary evaporator. The crude product is dissolved in 100 ml of pyridine and treated at 0°–5° C. with 200 ml of a ca 1 molar solution of chromium trioxide in pyridine/water (10:1 vol/vol). After stirring at 25° C. for 4 hours, the mixture is treated with 5 ml of ethanol and concentrated on a rotary evaporator. The residue is treated with 500 ml of ether and 300 ml of water and filtered under suction over Speedex. The organic phase of the filtrate is washed with water, dried over sodium sulphate and concentrated on a rotary evaporator. The residue obtained is adsorbed on 500 g of silica gel. Elution with methylene chloride containing 0.5–1% of methanol yields 10.5 g of pure 3,3-ethylenedioxy-D-homo-19-norpregn-5(10),17-dien-20-one, melting point 147°–148° C. (from ether/hexane); $[\alpha]_{589}^{25}$ = +238° (c = 0.101 in dioxane), which can be converted by acidic hydrolysis into D-homo-19-norpregna-4,17-diene-3,20-dione.

EXAMPLE 9

A solution of 5.5 g of D-homo-19-norpregn-4-ene-3,20-dione in 80 ml of orthoformic acid ethyl ester is treated at 0° C. with 5 ml of ethanol and with 0.6 g of solid p-toluenesulphonic acid. After 90 minutes, the mixture is treated with aqueous bicarbonate solution and worked-up with ether in the usual manner. The crude enol ether is dissolved in 40 ml of tetrahydrofuran and treated with 20 ml of tert.butanol, 40 ml of dimethylformamide and 3 ml of trimethylphosphite. The solution is cooled to −25° C., treated with 1.4 g of potassium tert.butylate and stirred in an oxygen atmosphere for 30 minutes. The mixture is poured on to ice-water, treated with 4 ml of 30% hydrogen peroxide and worked-up with ether in the usual manner. The crude product is dissolved in 100 ml of methanol, treated with 10 ml of 1-N aqueous hydrochloric acid and stirred at 25° C. for 80 minutes. After neutralisation with ammonium hydroxide, the methanol is removed on a rotary evaporator and the aqueous residue worked-up with methylene chloride in the usual manner. After chromatography on silica gel, there is obtained 17a-hydroxy-D-homo-19-norpregn-4-ene-3,20-dione; UV: $\lambda_{max}$ = 240 nm ($\epsilon$ = 17100).

The starting material can be prepared as follows:

3,3-Ethylenedioxy-D-homo-19-norpregna-5(10),17-dien-20-one (prepared according to Example 8) is reduced by means of lithium in ammonia and subsequently hydrolysed to D-homo-19-norpregn-4-ene-3,20-dione by means of aqueous hydrochloric acid.

EXAMPLE 10

Anhydrous hydrogen chloride gas is conducted for 5 seconds into a solution of 0.44 g of 17a-methyl-D-homo-19-norpregn-4-ene-3,20-dione and 0.34 g of dichlorodicyanobenzoquinone in 20 ml of dioxane. The mixture is held at 25° C. for 60 minutes and then filtered under suction over a paper filter. The filtrate is diluted with ether and washed with water. Working-up in the usual manner yields, after chromatography on silica gel, 17a-methyl-D-homo-19-norpregna-4,6-diene-3,20-dione; UV: $\lambda_{max}$ = 281 nm ($\epsilon$ = 23100).

We claim:

1. A D-homosteroid of the formula

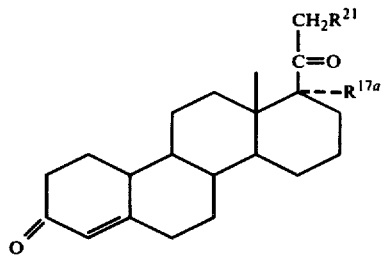

wherein $R^{17a}$ is hydroxy, lower alkoxy or acyloxy and $R^{21}$ is hydrogen, wherein said acyloxy is derived from a hydrocarbon monocarboxylic acid containing 1 to 10 carbon atoms.

2. A compound of claim 1 wherein $R^{17a}$ is an alkanoyloxy group containing from 1 to 7 carbon atoms.

3. The compound of claim 2 which is 17a-acetoxy-19-nor-D-homo-4-pregnene-3,20-dione.

4. The compound of claim 2 which is 17a-hexanoyloxy-19-nor-D-homo-4-pregnene-3,20-dione.

5. The compound of claim 1 which is 17a-hydroxy-D-homo-19-nor-pregn-4-ene-3,20-dione.